United States Patent

Bonometti et al.

[11] Patent Number: 5,185,268
[45] Date of Patent: Feb. 9, 1993

[54] METHOD FOR THE DETERMINATION OF TOTAL NITROGEN INCLUDING ADDING AN ALKALI METAL HALIDE OR AN ALKALINE EARTH METAL HALIDE TO THE SAMPLE

[75] Inventors: Bonometti; Roland Olivier, both of Orthez; Jacques Maurice, Pau, all of France

[73] Assignee: Societe Nationale Elf Aquitaine, France

[21] Appl. No.: 640,961

[22] Filed: Jan. 14, 1991

[30] Foreign Application Priority Data

Jan. 12, 1990 [FR] France .................................. 90 00312

[51] Int. Cl.⁵ .............................................. G01N 21/76
[52] U.S. Cl. ..................................... 436/114; 436/115
[58] Field of Search ................. 436/106, 111, 114, 115

[56] References Cited

U.S. PATENT DOCUMENTS

| | | | |
|---|---|---|---|
| 3,877,875 | 4/1975 | Jones et al. | 436/114 X |
| 4,018,562 | 4/1977 | Parks et al. | 436/114 |
| 4,066,402 | 1/1978 | Komiyama et al. | 436/115 |
| 4,066,409 | 1/1978 | Fine | 436/114 |
| 4,333,735 | 6/1982 | Hardy et al. | 436/114 |

Primary Examiner—Robert J. Hill, Jr.
Attorney, Agent, or Firm—Ostrolenk, Faber, Gerb & Soffen

[57] ABSTRACT

A method of determining nitrogen in various nitrogenous materials, wherein the materials are combusted by being brought into contact with a solid metallic catalytic mass, in the presence of an oxygenated gas, so as to convert the nitrogen into NO. This is then determined, preferably by chemiluminescence or by optical interferometry. The method is improved by adding a halide of an alkali metal or an alkaline earth metal to the materials prior to combustion.

An apparatus comprising an oven (1,2,2') charged with catalytic mass (4), which can be a wire acting as a heating element, and provided with an oxygen inlet (6). The catalytic mass is a non-oxidizable ferrous alloy or a metal of the Pt group.

17 Claims, 1 Drawing Sheet

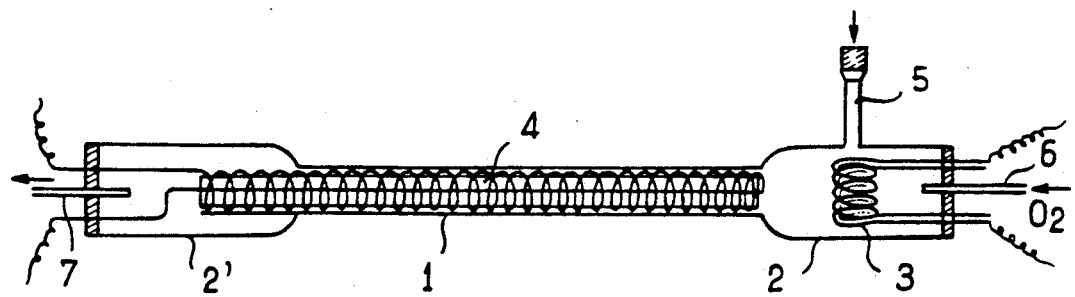
FIG_1
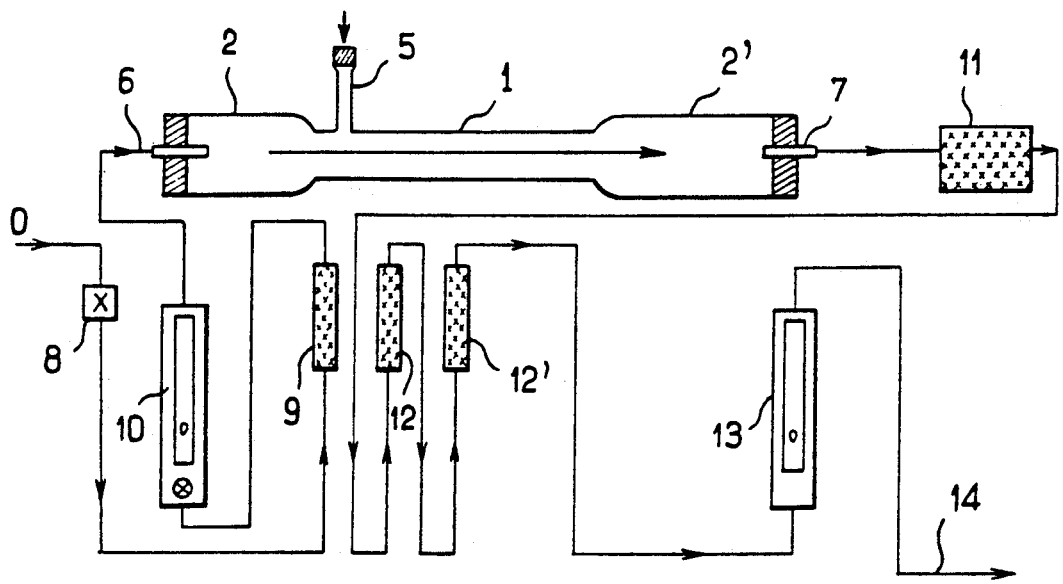
FIG_2
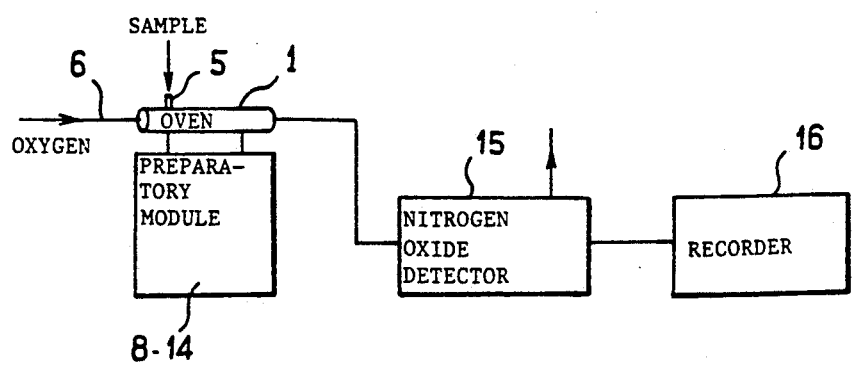
FIG_3

METHOD FOR THE DETERMINATION OF TOTAL NITROGEN INCLUDING ADDING AN ALKALI METAL HALIDE OR AN ALKALINE EARTH METAL HALIDE TO THE SAMPLE

The invention relates to the rapid determination of total nitrogen in various media, especially in waste waters and the like. It comprises a novel method of performing such analyses, as well as an apparatus for carrying it out. This method and this apparatus are particularly useful for the permanent monitoring of pollution in urban or industrial waters; it provides an easy way of assessing total nitrogen contents as low as 100 ppb, for example, with great rapidity, irrespective of the chemical form in which this nitrogen is present.

The well-known classical method, which gives accurate and constant results, is the KJELDAHL method based on attack of the sample with sulfuric acid, followed by titration of the ammonia released from the sulfuric acid solution under the action of an alkaline base. However, between the moment of sampling and the result of the analysis, there is a period of several hours during which the operations demand the continual attention of a manipulator; it is therefore impossible to conduct a constant monitoring process producing quantitative data at any time. As regards the method which consists in operating in the same way as for the determination of total carbon, it gives very variable results according to the chemical nature of the nitrogenous compounds present, some of which are almost completely missed; this is the case, for example, of amino alcohols and amino acids.

The present invention provides an important improvement in this area by making it possible to follow the total nitrogen content of a given medium very rapidly; the results are easy to record and can represent dozens of analyses a day.

In the method according to the invention, which comprises combusting the nitrogenous materials in a sample, a volatilized sample of the compounds to be determined is brought into contact with one or more metallic catalytic masses heated to high temperature, in the presence of oxygen, so as to convert the nitrogenous compounds in the sample into NO and subsequently to determine the amount of NO formed, by a method known per se.

The nature and area of the metal surface of the heated catalyst play an important part in the method of the invention: the metal is non-oxidizable, such as Fe-Ni or Fe-Ni-Cr steel which may or may not contain V, Mo, W, Co, Nb, Ti etc. The heating element can be made of W or an alloy of this metal, especially with one or more of the above-mentioned metals. Suitable metals are those of the platinum group, Pt-Ir etc., and very particularly platinum rhodium, for example 90% Pt/10% Rh, preferably in the form of wires acting as a heating element.

The method is carried out in such a way that the contact with the gas phase passed over the heated catalyst is as intimate as possible; to achieve this, the thickness of the gaseous layer brought into contact with the metal is preferably no more than 3 mm and more preferably between 0.3 mm and 2 mm, particularly between 0.5 and 1.5 mm.

The contact time between the catalyst and the gas stream carrying the materials to be analyzed, at temperatures of the order of 800° to 1200° C., is generally 0.2 to about 3 seconds; at the preferred temperatures of 900° to 1000° C., it is desirable for this contact time to be of the order of 0.5 sec to 2 sec and especially 0.5 to 1 sec. Conversely, if it is desired to perform the analysis in 10 to 30 sec, for example, the surface area of the metal, in particular PtRh, should be 5 to 40 $cm^2$ and preferably 7 to 9 $cm^2$.

Thus, according to the invention, the nitrogenous compounds, whatever they may be, are converted solely into NO by virtue of the catalytic effect of the metal over which they are passed at high temperature. According to one particular embodiment, the heating can be effected by an appropriate means other than by passing a current through the catalytic metal; alternatively, this external heating is auxiliary to that produced by the catalytic metal itself.

If the sample to be analyzed is introduced into the hot catalytic space in the form of a solution, this can be aqueous or organic; in other words, the nitrogenous compound or compounds are dissolved or dispersed in water or in an organic solvent, for example an alcohol, ketone, ester, hydrocarbon or the like, with the exclusion, of course, of amines, amides and other nitrogenous compounds. As soon as it is introduced into the hot analytical zone, this solution is evaporated and its vapor is entrained by a stream of air or oxygen through a heated catalytic region. Entrainment with oxygen is particularly practical.

Although the treatment of aqueous solutions is highly convenient, especially where the continuous monitoring of industrial or urban waters is concerned, the invention also applies to solid or pasty samples provided they can be volatilized under the action of heat in a stream of oxygenated gas. In this case, the solid sample is placed in a boat at the entrance to an appropriate oven and subjected to the gas stream in exactly the same way as liquid samples.

According to a special embodiment of the invention, it has become possible greatly to improve the accuracy of the analysis by the addition of an electrolyte to the sample of material to be analyzed. More particularly, the accuracy is increased by the introduction of a halide, especially an alkali metal or alkaline earth metal fluoride, chloride or bromide. Although the amount of electrolyte to be used is not critical, it is convenient to add about 0.01 to 0.2 equivalent thereof per liter of solution to be analyzed, the preferred proportion generally being of the order of 0.05 to 0.15 eq. For practical reasons, salts such as NaCl, KCl, $CaCl_2$ and/or $MgCl_2$ are particularly suitable. In the case of NaCl, excellent results are obtained with 3 to 7 g per liter, although successful results can be obtained using about 1 to 10 g/l. With 5 g/l in the determination of amino alcohols in an aqueous medium, the accuracy of the results improved from ±8% to ±1.6%, which is remarkable in view of the difficulties of determining this kind of compound.

Hydrohalic acids also have the effect of improving the accuracy of the measurements, but, as their use results in acidification of the gas stream and the release of halogen, both of which are detrimental to the apparatus, it becomes necessary to carry out a subsequent neutralization. It is therefore much more practical to use the aforementioned neutral salts.

According to the invention, after the nitrogenous compounds have been converted into the oxide NO, the latter is determined by any method known per se. A very suitable method is the chemiluminescence produced by the reactions

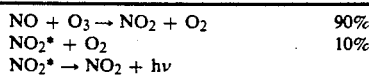
| | |
|---|---|
| $NO + O_3 \rightarrow NO_2^* + O_2$ | 90% |
| $NO_2^* + O_2$ | 10% |
| $NO_2^* \rightarrow NO_2 + h\nu$ | | used in the apparatus from SERES and ENVIRONNEMENT S.A. Another good method is based on optical interferometry (SERES apparatus, ELF-ANVAR licence). As these methods are known in the art, it is not appropriate to describe them here.

In the apparatus according to the invention, which comprises an oven with means of heating to 800° C. or above, and means of blowing an oxygenated gas into this oven, the oven contains a charge of catalyst for the selective oxidation of nitrogenous compounds to the oxide NO; the apparatus has a device for determining the NO in the gas which has passed through the oven.

The enclosure of the oven, which is generally tubular, is made of refractory material such as porcelain, alumina, quartz or the like, or of metal, for example stainless steel. It is heated externally by means of an electric coil or a gas, internally by means of a heating resistance element or rod, or, if appropriate, both externally and internally.

As an essential characteristic of the apparatus is the presence of an appropriate catalyst in the path of the gas passed through the oven, this catalyst is arranged in the enclosure of the oven so as to be in the most intimate contact possible with the gas. Thus a catalytic mass can fill all or part of the enclosure; it can be in the form of beads, rings, chips, filaments or other pieces made of the different catalytic metals indicated above.

In the particular case of simultaneous external and internal heating, wires or fibers of catalytic metal can surround an axial heating rod.

One very advantageous embodiment, which has given remarkable results, consists in using wires of catalytic metal both as catalyst and as electrical heating resistance element. It has been particularly successful with platinum rhodium containing 10% of Rh.

Another characteristic of the apparatus of the invention is the provision of a volatilization chamber at the entrance to the oven; the purpose of this chamber is to receive the sample to be analyzed and heat it to the high temperature at which it becomes possible for the stream of oxygenated gas to entrain it towards the interior of the oven. Preferably, the heating system for the volatilization chamber is independent of that for the rest of the oven and, consequently, separately adjustable.

In the case mentioned above, where the heating element itself acts as the catalytic mass, separate turns housed in the volatilization chamber serve to heat the sample introduced into this chamber to the appropriate temperature. If the sample is an aqueous or organic solution, one embodiment according to the invention makes provision for a nozzle at right angles to the volatilization chamber, making it possible to introduce an injection tube or needle for bringing the sample substantially into the middle of the heating element in the chamber; preferably, a network of refractory fibers, especially asbestos fibers, is then placed inside the heating turns to give a good distribution of the sample in the volatilization chamber.

BRIEF DESCRIPTION OF THE DRAWINGS

By way of a non-limiting example, an embodiment of the apparatus according to the invention is described below with reference to the attached drawings.

FIG. 1 shows the oven of the apparatus in axial section;

FIG. 2 schematically shows the oven with its accessories forming the preparatory module of the apparatus; and FIG. 3 is a chart of the whole system.

FIG. 1 shows the tubular quartz oven consisting of a tube 1 terminated at its ends by widened parts or "tulips" 2 and 2'. Arranged in the tulip 2 are turns 3 made of Pt containing 10% of Rh, with asbestos fibers placed between them. Also, the tulip 2 carries a side nozzle 5 through which the liquid sample is introduced by means of a microsyringe; the length of the latter is chosen to be sufficient for its tip to penetrate into the middle of the assembly of turns 3, where the asbestos distributes the injected liquid well and cleans the end of the needle.

An oxygen-carrying tube 6 passes through the stopper which seals the tulip 2 at the rear, said oxygen being blown towards the inside of the oven throughout the analysis. A second heating element 4, similar to 3, wound around a porcelain rod, occupies the whole length of the part 1 of the oven and terminates inside the tulip 2'. The drawing shows the terminals of the two heating elements, which lead to electrical sockets and regulating devices in known manner.

FIG. 2 shows how the oxygen, which enters the oven at 6, is admitted via a valve 8 and then passes through a drying column 9 and a flow meter 10 before arriving at 6.

At the outlet 7 of the oven, the gases pass through a layer of adsorbent silica (silica gel) in the interchangeable tube 11 and then through the drying columns 12-12' and a flow meter 13, from which they are passed into a nitrogen oxide analyzer 15 (FIG. 3) via a line 14.

The whole analytical installation is represented by the chart in FIG. 3. The NO detector used, denoted by 15, was in particular a chemiluminescence or optical refractometry apparatus. A classical recorder 16 terminated the system.

ANALYTICAL EXAMPLES

The method and apparatus described were applied to the determination of total nitrogen in a series of aqueous solutions of various nitrogenous compounds and to the waste waters from a factory. The apparatus had the following characteristics:

diameter of each turn of the resistance element (3) in the volatilization chamber (2): about 5 mm;
caliber of the Pt-Rh wire forming this resistance element (3): 5/10
total length of this wire (3): 28 cm
internal diameter of the quartz tube (1): 8 mm
diameter of the turns (4) housed in this tube: 5 mm
length of the part (1) of the oven: 14 cm
total length of the Pt-Rh wire in the part (1): 90 cm
The temperature inside the oven was 900° to 1000° C.
5 to 20 µl of sample solution were injected at (5).
The oxygen flow rate was adjusted to about 13 l/h.
The response time was 25 sec.
The measurement range was situated between 0.1 and 20 mg/l, expressed as elemental nitrogen (N).

The Table below gives the analytical results for different nitrogenous compounds: an average accuracy of about ±8% is found.

In another series of analogous measurements, but after the addition of 5 g of NaCl to the sample solutions, the accuracy comes out at ±1.6%.

TABLE

| Composition of the mixture | Concentration N mg/l | Results | |
|---|---|---|---|
| | | Chemi-luminescence | Liquid chromatography Colorimetry |
| $NH_4Cl$ + | 5 | 4.50 | 4.48 |
| $NaNO_2$ | 10 | 9.35 | 9.69 |
| $NH_4Cl$ + | 5 | 4.05 | 4.2 |
| DEA | 10 | 9.25 | 9.55 |
| $NaNO_3$ + | 5 | 4.9 | 4.3 |
| DEA | 10 | 10.0 | 10.15 |
| $NaNO_3$ + | 5 | 4.85 | 4.95 |
| DEA + | 10 | 9.80 | 9.15 |
| $NH_4Cl$ | | | |
| $NaNO_3$ | 5 | 5.2 | 4.84 |
| DEA | 10 | 10.55 | 10.9 |
| $NH_4Cl$ | | | |
| $NaNO_2$ | – | | |

Note: DEA denotes diethanolamine.

What is claimed is:

1. A method of determining total combined nitrogen in nitrogenous materials which comprises contacting a volatilized admixture of a volatilized sample of a material to be analyzed which contains a halide of an alkali metal or alkaline earth metal when it is volatilized and an oxygen containing gas with a metallic oxidation catalyst at a temperature sufficient to convert all nitrogenous material in the sample into NO, and determining the amount of NO thus formed, whereby the amount of total combined nitrogen can be calculated from the determined amount of NO thus formed.

2. A method according to claim 1 in which the catalyst comprises a metal selected from the group consisting of V, Mo, W, Co, Nb and Ti.

3. A method according to claim 1 in which the catalyst comprises a metal of the platinum group.

4. A method according to claim 3 in which the catalyst is Pt-Ir or Pt-Rh.

5. A method according to claim 3 in which the catalyst is platinum-rhodium containing about 10% rhodium.

6. A method according to claim 1 in which the catalyst comprises a wire acting simultaneously as an electrical heating element.

7. A method according to claim 1 in which the contacting temperature is 800° to 1200° C.

8. A method according to claim 7 in which the contacting temperature is 900° to 1000° C.

9. A method according to claim 1 in which the contacting is done by flowing the volatilized admixture such that it remains in contact with the catalyst for 0.2 to 3 seconds.

10. A method according to claim 9 in which the temperature is 900° to 1000° C. and the contact time is 0.5 to 3 seconds.

11. A method according to claim 1 in which the sample of the material to be analyzed is in the liquid state and is volatilized and mixed with the oxygen containing gas to form the volatilized admixture.

12. A method according to claim 1 in which the sample of the material to be analyzed is in the form of a solution to which has been added 0.01 to 0.2 equivalent of said halide per liter and said solution is volatilized and combined with the oxygen containing gas to form the volatilized admixture.

13. A method according to claim 12 in which the amount of halide is 0.05 to 0.15 equivalent per liter.

14. A method according to claim 12 in which the sample of the material to be analyzed is an aqueous solution comprising aminoalcohol to which has been added 1 to 10 grams of sodium chloride per liter.

15. A method according to claim 12 in which the halide is an alkali metal halide.

16. A method according to claim 12 in which the halide is selected from the group consisting of sodium chloride, potassium chloride and calcium chloride.

17. A method according to claim 1 in which the halide is mixed with the sample prior to admixture with the oxygen containing gas.

* * * * *